United States Patent [19]

Lee

[11] Patent Number: 4,792,395
[45] Date of Patent: Dec. 20, 1988

[54] HIGH SPEED COUNTERCURRENT CENTRIFUGE FOR REMOVAL ATTACHMENT OF CHROMATOGRAPHIC COLUMNS THERETO, AND CHROMATOGRAPHIC COLUMN FOR THE SAME

[76] Inventor: David Y. W. Lee, 105 Highland Dr., Chapel Hill, N.C. 27514

[21] Appl. No.: 86,320

[22] Filed: Aug. 14, 1987

[51] Int. Cl.[4] .............................................. B01D 15/08
[52] U.S. Cl. .................................. 210/198.2; 210/657
[58] Field of Search ................... 210/657, 198.2, 198.3

[56] References Cited

U.S. PATENT DOCUMENTS

| | | | |
|---|---|---|---|
| 3,349,920 | 10/1967 | Waters | 210/198.2 |
| 3,775,309 | 11/1973 | Ito | 210/198.2 |
| 3,846,306 | 11/1974 | Barker | 210/198.2 |
| 3,994,805 | 11/1976 | Ito | 210/198.2 |
| 4,051,025 | 9/1977 | Ito | 210/198.2 |
| 4,058,460 | 1/1977 | Ito | 210/657 |
| 4,228,009 | 10/1980 | Ito | 210/198.2 |
| 4,287,061 | 9/1981 | Sutherland | 210/198.2 |
| 4,293,415 | 10/1981 | Bente | 210/198.2 |
| 4,321,138 | 3/1982 | Ito | 210/198.2 |
| 4,324,661 | 4/1982 | Ito | 210/657 |
| 4,430,216 | 2/1984 | Ito | 210/198.2 |
| 4,487,693 | 12/1984 | Ito | 210/657 |
| 4,532,039 | 7/1985 | Ito | 210/198.2 |
| 4,604,198 | 8/1986 | Dailey | 210/198.2 |
| 4,615,805 | 10/1986 | Ito | 210/198.2 |

*Primary Examiner*—Ernest G. Therkorn
*Attorney, Agent, or Firm*—Browdy and Neimark

[57] ABSTRACT

A high speed countercurrent centrifuge is designed so that the chromatographic column used therewith may be readily replaced. A shaft for rotating a chromatographic column includes a column holder plate fixed therearound. The column holder plate has upwardly extending pins which engage the corresponding holes on the bottom flange of a spool about which a chromatographic column is wrapped, fixing the orientation of the spool relative to the column holder plate. Also a multi-layer chromatographic column is constructed to be used in the centrifuge. Multiple layers of tubing are wrapped around the above-described spool. The inlet and outlet ends of this tubing terminate in tubing adaptors mounted on an outer surface of a flange to permit quick connection of the column to the flow tubes of the centrifuge apparatus.

7 Claims, 3 Drawing Sheets

HIGH SPEED COUNTERCURRENT CENTRIFUGE FOR REMOVAL ATTACHMENT OF CHROMATOGRAPHIC COLUMNS THERETO, AND CHROMATOGRAPHIC COLUMN FOR THE SAME

FIELD OF INVENTION

This invention relates to high speed countercurrent chromatography with a multiple layer coiled column. The present invention relates more particularly to a system for continuous countercurrent chromatography using a disposable multiple layer coiled column which is separated from the gear, holding and mounting system and can be removed and changed independently and safely.

BACKGROUND OF THE INVENTION

Various types of coil planet centrifuges have been developed for separating solutes and/or particles on the basis of partition coefficients and/or elutriation. Among the various systems, the high speed countercurrent chromatography with a multiple layer coiled column (see U.S. Pat. No. 4,430,216 to Y. Ito, incorporated herein by reference) represents the most efficient system in terms of speed, resolution and capacity. However, the multiple layer coiled column is an integral part of gear, holding and mounting assembly, difficult to remove and expensive to replace. The advantage of altering the size (length and diameter) of the multiple layer coiled column to meet specific sample requirements was therefore seriously limited. Additionally, the expense of column replacement seriously limited the usefulness of countercurrent chromatography using toxic or radioactive materials. An easily detachable and disposable multiple layer coiled column would greatly improve the versatility and capability of the high speed countercurrent chromatography system and to provide a more useful, economical and convenient tool in countercurrent separations.

SUMMARY OF THE INVENTION

Accordingly, a main object of the present invention is to overcome the disadvantage and inconvenience of previously employed multiple layer coiled column in high speed countercurrent chromatography. A further object of the invention is to provide a safely detachable multiple layer coiled column which is separated from gear, holding and mounting system of the apparatus. A still further object of the invention is to provide an economical and disposable multiple layer coiled column for countercurrent chromatography of hazardous and/or radioactive materials. A still further object of the invention is to provide a novel and improved apparatus for preparative or analytical separation in high speed countercurrent chromatography. A still further object of the invention is to provide a convenient and economical apparatus for performing continuous extraction of chemicals and separation of particles, which includes separation and purification of protein, cells and bioengineering products.

The foregoing objectives are achieved in accordance with the present invention by providing a novel multiple layer coiled column system which is separated from a permanently mounted rotating gear and holding unit and can be replaced easily and safely. The system is integrated with a weight-adjustable counterweight and means for achieving the planet and centrifuge motions.

BRIEF DESCRIPTION OF THE DRAWINGS

Further objects and advantages of the invention will become apparent from the following description and the accompanying drawings wherein.

DETAILED DESCRIPTION OF PREFERRED EMBODIMENTS

The principle and scheme to subject a multi-layer coiled column under synchronous planetary motion as utilized in the present invention is exemplified in connection with the high speed preparative countercurrent chromatography with a multi-layer coiled column (see the aforementioned U.S. Pat. No. 4,430,216 to Y. Ito; and Y. Ito, J. Chromatography 214 (1981) 122).

Figure 1:
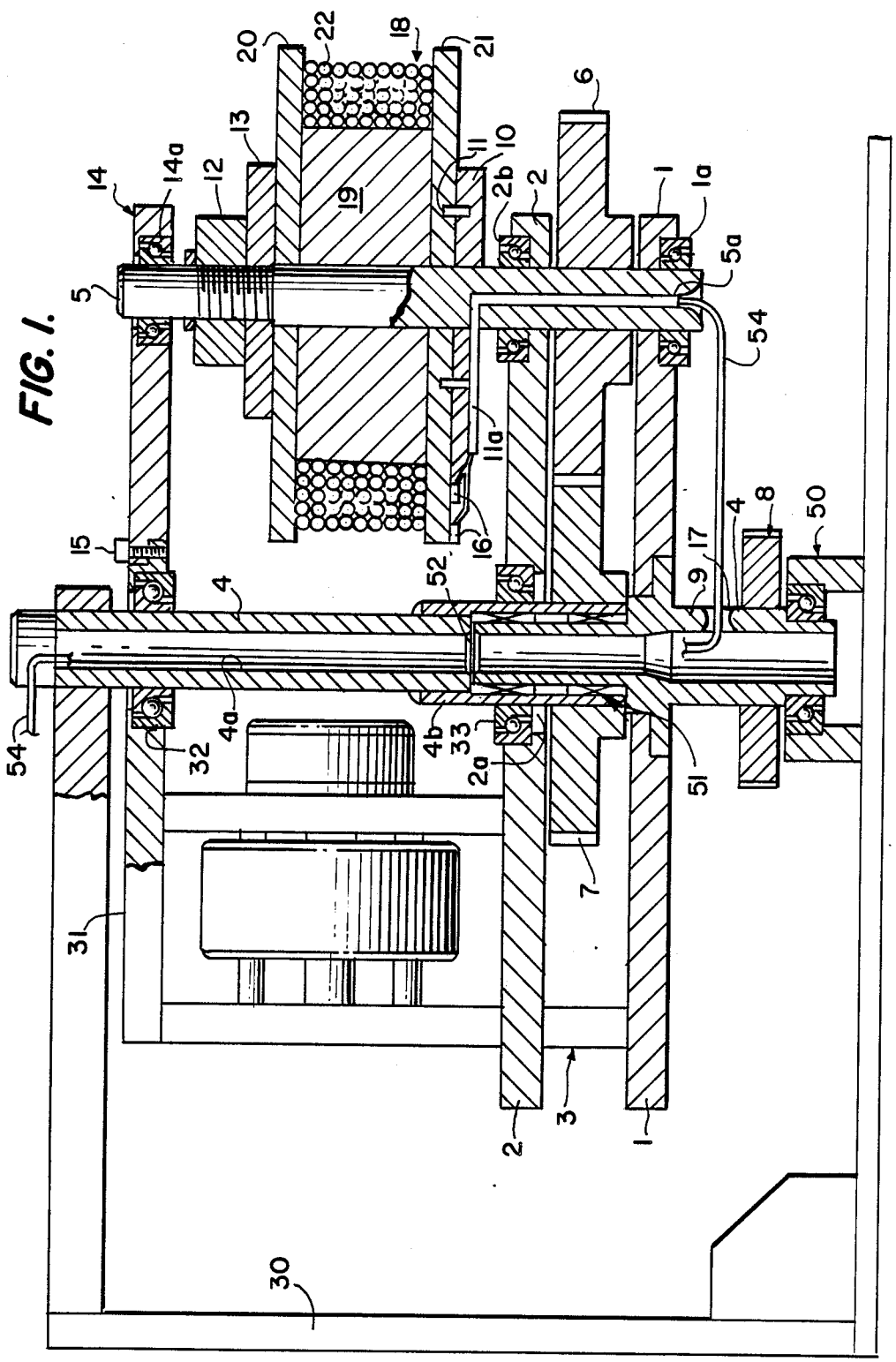
FIG. 1 is a vertical cross-sectional view of a high speed countercurrent chromatography apparatus according to the present invention.
Figure 2:
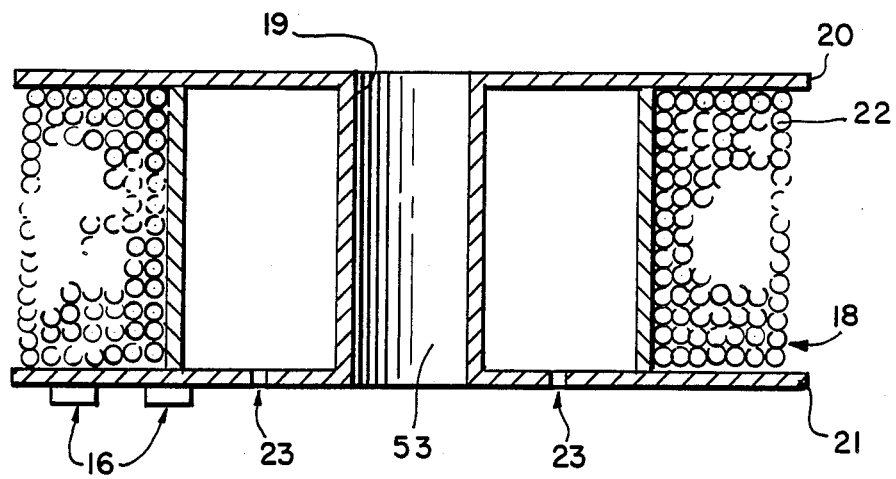
FIG. 2 is an enlarged cross-sectional view of the new multiple layer coiled column with removable flow tubing adaptors and mounting holes.

As illustrated in FIGS. 1 and 2, an illustrative embodiment of a high speed countercurrent chromatography apparatus according to the present invention, includes a main support 30 and a frame composed of two spaced-apart, horizontal, circular first and second plates, 1, 2. Plate 2 has a central bore 2a, with bearing 33 surrounding sleeve 4b fixed about stationary pipe 4. A plurality of tubular spacers 3 are positioned between the plates 1 and 2. The frame is mounted to rotate around a stationary pipe 4, which forms the central axis of the apparatus. The frame supports a rotary shaft 5, which is fixed to a planetary gear 6 in between the circular plates 1 and 2, and is spaced apart from stationary pipe 4. Rotary shaft 5 rotates within bearings 1a and 2b, respectively. The planetary gear 6 is in mesh with an identical stationary sun gear 7 rigidly mounted on the central stationary pipe 4. This gear arrangement causes rotary shaft 5 to undergo a synchronous planetary motion when a motor drives the frame through a gearbelt drive 8 and a short coupling pipe 9. Short pipe 9 rotates on pedestal bearings 50 and needle roller bearings 51. The stationary section, 4, does not rotate with lower section 9 by virtue of bearings 52. The column holder 10 is rigidly mounted on the rotary shaft 5 and is equipped with four pins 11 and flow tube channel 11a. A pair of quick release nuts 12, 13 are used to secure the multilayer coiled column. Top support plate 31 has a removable top bearing and holding section 14 (which includes top bearing 14a) secured onto the central shaft by a removable (preferably quick releasing) screw 15 which provides a guide release of the top bearing and holding portion 14 from the remainder (i.e., fixed portion) of support plate 31. The remainder of support plate 31 houses bearings 32.

The flow tubes are detachable from tubing adaptors 16 which is permanently mounted on the flange of the reel. The flow tubes 54 are passed downwardly through the central bore 5a of the shaft 5; upwardly through the bore 4a of the stationary pipe 4, thereby exiting from the top of the centrifuge.

FIG. 2 generally designates a typical design of an improved multi-layer coiled column 18. The multiple-layer coiled column 18 is prepared by winding a long piece of PTFE tubing tightly around the spool 19 between the retaining flanges of the spool shown at 20, 21, to form multiple layers of the coil 22 up to the rims of the flanges, cocentrically with respect to a hollow cylindrical center 53, for receiving shaft 5, the terminals of the column being connected to respective flow tubes through a set of tubing adaptors 16 at the bottom of the flange. There are four pin-holes 23 on the bottom side of the bottom flange for positioning onto pins 11 the column holder 10 (FIG. 1). The juxtaposition of pins 4 with pinholes 23 fixes the orientation of column 18 and spool 19 with respect to column holder 10.

The tubing adaptor may be any of a variety of well-known means for permitting quick assembly and disassembly of tubing. For example, the tubing adaptor may include a threaded male or female extension which couples with a corresponding threaded female or male terminal of a flow tube. Generally, in such an arrangement, the male connector is crimped about a flow tube and the female connector is in two pieces. The first piece, an unthreaded flanged sleeve, is crimped about the flow tube, while the second piece, which is internally threaded, has a collar of smaller diameter than the flange of the sleeve at its end opposite the end connecting to the male piece, but otherwise is of a larger diameter than the sleeve. Thus, tightening of the connectors prevents leaks.

Figure 3:
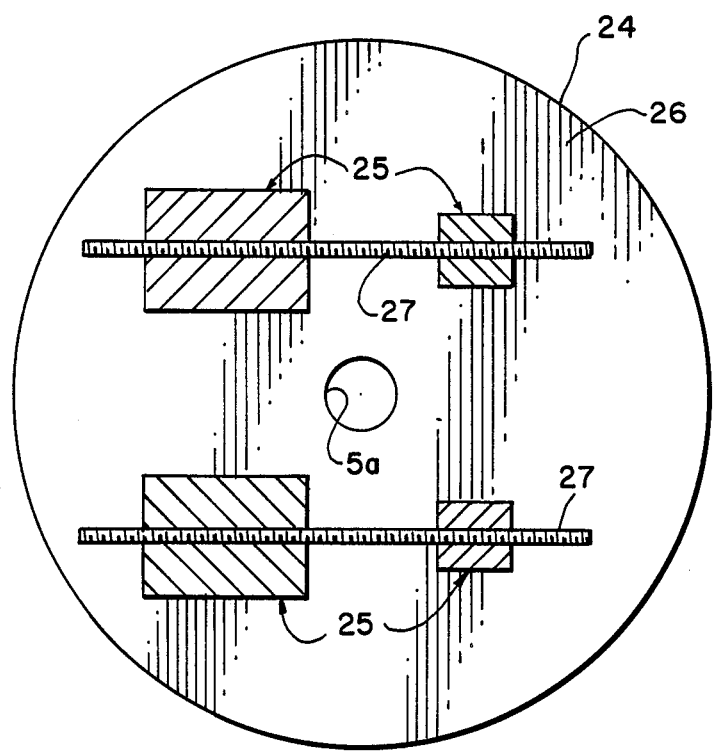
FIG. 3 is a top plan view of the counterweight

FIG. 3 shows a new design of the counterweight 24 which is a round metal disk 26 equipped with a set of weights 25 adjustable horizontally via screw motions along rods 27. The counterweight 25 is mounted on a rotary shaft 5b opposite rotary shaft 5. Of course, the present invention may employ conventional balancing, such as a dummy column. If a dummy column is employed, the dummy column is preferably attached to the central shaft and the frame in a manner analogous to the attachment of spool 19 to shaft 5 and the frame. Thus, the dummy weight may be easily replaced whenever the spool 19 and column 22 assembly are replaced.

Figure 4:
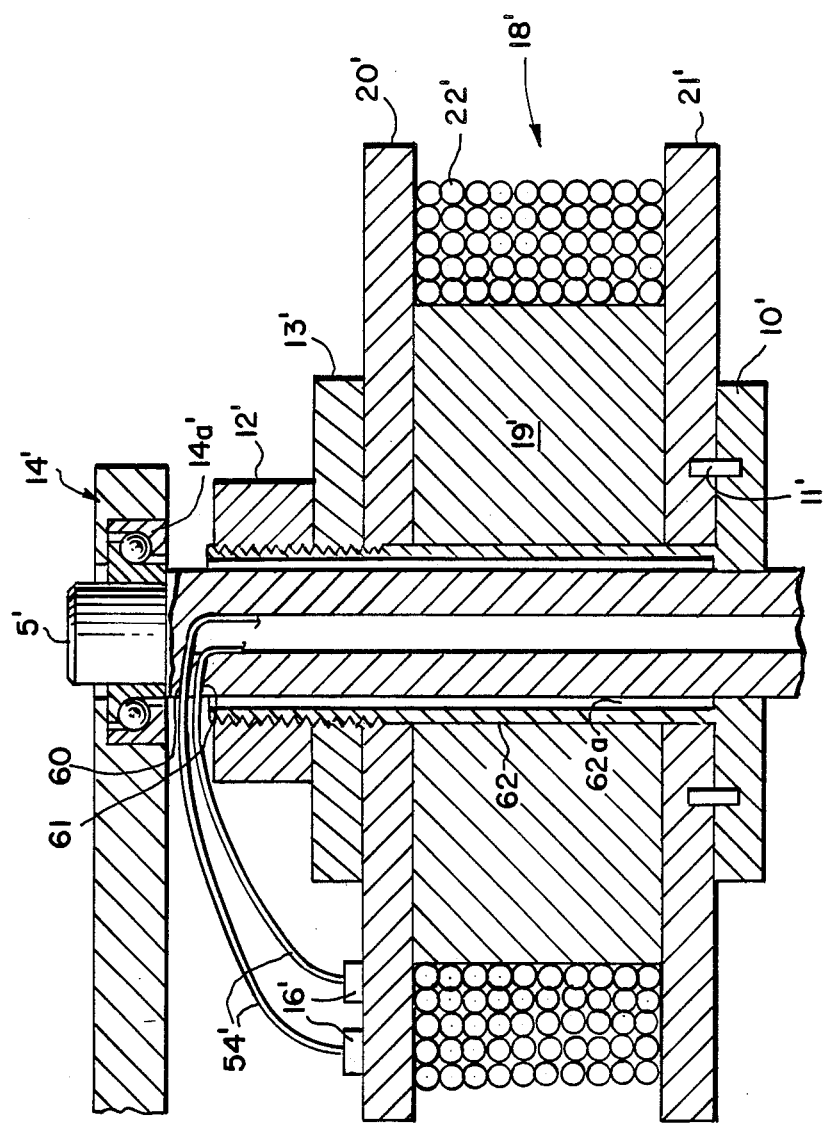
FIG. 4 shows an alternative embodiment for the attachment of the spool, shaft and flow tubes.

FIG. 4 shows a variation of the column holder arrangement used in the present invention. Elements 5′ 10′ 11′, 12′, 13′, 14′, 14a′, 16′, 18′, 19′, 20′, 21′, 22′ and 54′ correspond, respectively, to the corresponding elements 10, 11, 12, 13, 14, 14a, 16, 18–22 and 54 in the embodiment of FIGS. 1–3 and will not be further described in detail. In this embodiment, a sleeve 62 is fitted around central shaft 5′. Thus, flow tubes 54′ can extend upwardly through a central bore in shaft 5′, and out through exits 60 and 61, finally connecting to top flange 20′ and tubing adaptors 16′. Quick release nuts 12′ and 13′ are screw threaded about sleeve 62. Sleeve 62 is fixed to or is monolithic with column holder 10′. The embodiment of FIG. 4, which places the tubing connections 16′ at the top of spool 19′, permits facile inspection of the flow tubes 54′ and their connections. Sleeve 62 is necessary to create space 62a so that the column 18′ may be slid off shaft 5′ without hindrance by the portion of tubes 54′ extending through opening 60.

It should be understood that terms such as "top" and "bottom", as used throughout the specification and claims, refer only to the orientation of various elements relative to each other, and not to the absolute orientation of any one element in space.

The revolutional speed of the apparatus can be regulated continuously up to 2000 rpm by employing a speed control unit with digital readout. In a typical embodiment, the apparatus was in the form of a compact table model. The solvents were pumped by means of two separate piston pumps. The inlets and outlets of the flow tubes were designated with colors for easy identification. It is understood that when the apparatus rotated at a high revolution speed it can be disposed in any orientation with respect to the earth. If desired, the inside surface of the chromatographic tubing may be coated with a biopolymer or bioligand typically used for separating biological products.

While certain specific embodiments have been disclosed in the foregoing description, it will be understood that various modifications within the scope of the invention may occur to those skilled in the art. Therefore, it is intended that adaptions and modifications should and are intended to be comprehended within the scope of the appended claims.

What is claimed is:

1. An apparatus for high speed countercurrent chromatographgy comprising:

a frame including a first bottom plate mounted for rotation about a pipe extending between said first bottom plate and a top supporting plate of said frame, a fixed portion of said top supporting plate surrounding said pipe and extending outward therefrom to at least one side being fixed by a connecting member to said first bottom plate, a detachable portion of said top supporting plate being releasably attached to said fixed portion;

releasing means for releasably mounting said detachable portion to said fixed portion;

a shaft, parallel to and spaced apart from said pipe, extending rotatably between said first bottom plate and said detachable portion, said shaft extending through a bore of a bearing section in said detachable portion;

a plate-shaped column holder rigidly fixed to and extending radially away from said shaft, said column holder having means for receiving a spool on a radially extending surface thereof in a manner which prevents rotation of the spool with respect to said shaft and said column holder;

means for rotating said frame about said pipe;

means for transmitting the rotation of said frame to said shaft;

a second bottom plate fixed to said frame below said first bottom plate, said pipe including a first section extending through said first and second bottom plates, said first section of said pipe being rotatable with respect to said first bottom plate but not with respect to said second bottom plate, and a second section between said top supporting plate and above said first bottom plate, said top supporting plate and said first section of said pipe being rotatable with respect to said second section of said pipe, said second section extending through and being rotatable with respect to said second bottom plate and said shaft extending through said second bottom plate;

and wherein said rotating and transmitting means collectively comprise:

a sun gear fixed to and extending radially away from said pipe, positioned between said first and second bottom plates; and a planetary gear fixed to and extending radially away from said shaft, positioned between said first and second bottom plates, and said planetary gear meshing with said sun gear.

2. An apparatus for high speed countercurrent chromatography comprising:
- a frame including a first bottom plate mounted for rotation about a pipe extending between said first bottom plate and a top supporting plate of said frame, a fixed portion of said top supporting plate surrounding said pipe and extending outward therefrom to at least one side being fixed by a connecting member to said first bottom plate, a detachable portion of said top supporting plate being releasably attached to said fixed portion;
- releasing means for releasably mounting said detachable portion to said fixed portion;
- a shaft, parallel to and spaced apart from said pipe, extending rotatably between said first bottom plate and said detachable portion, said shaft extending through a bore of a bearing section in said detachable portion;
- a plate-shaped column holder rigidly fixed to and extending radially away from said shaft, said column holder having means for receiving a spool on a radially extending surface thereof in a manner which prevents rotation of the spool with respect to said shaft and said column holder;
- means for rotating said frame about said pipe;
- means for transmitting the rotation of said frame to said shaft;
- and a spool having a central bore for being slidably received on said shaft, said spool also having a top and bottom flange, said spool being secured to said column holder by at least one quick-release means adjacent to said surface screw-threaded around said shaft above one of said flanges, an outer surface of the other of said flanges being supported upon said column holder.

3. The apparatus of claim 2, wherein said means for receiving a spool comprises a plurality of axially extending pins or openings, and wherein an outer surface of said other flange has a plurality of corresponding pins or openings for receiving said plurality of pins or openings.

4. The apparatus of claim 2, wherein said releasing means comprises a removable screw.

5. The apparatus of claim 2, wherein said spool has a piece of tubing, with two ends, wrapped thereabout, each said end of said tubing terminating on an outer surface of one of said flanges of said spool in a tubing adaptor distinct from that of the other end for detachably receiving a flow tube from outside said spool.

6. The apparatus of claim 5, further comprising dynamic counterbalancing means positioned opposite said spool, between said top supporting plate and said first bottom plate, for dynamically balancing said apparatus.

7. The apparatus of claim 5 wherein said tubing is wrapped in multiple layers around said spool.

* * * * *